United States Patent
Stoor et al.

(12)

(10) Patent No.: US 6,342,207 B1
(45) Date of Patent: Jan. 29, 2002

(54) METHOD FOR REDUCING THE VIABILITY OF DETRIMENTAL ORAL MICROORGANISMS IN AN INDIVIDUAL, AND FOR PREVENTION AND/OR TREATMENT OF DISEASES CAUSED BY SUCH MICROORGANISMS; AND WHITENING AND/OR CLEANING OF AN INDIVIDUAL'S TEETH

(76) Inventors: Patricia Stoor, Sirkkalankatu 11 B b 29, FIN-20500 Turku; Eva Soderling, Hiihtolantie 7, FIN-21290 Rusko; Antti Yli-Urpo, Värttinäkatu 17, FIN-20660 Littoinen; Jukka Salonen, Puolalausuisto 4bA4, FIN-20100 Turku, all of (FI)

( * ) Notice: Subject to any disclaimer, the term of this patent is extended or adjusted under 35 U.S.C. 154(b) by 0 days.

(21) Appl. No.: 09/690,810

(22) Filed: Oct. 18, 2000

Related U.S. Application Data

(62) Division of application No. 09/260,081, filed on Mar. 2, 1999, now Pat. No. 6,190,643.

(51) Int. Cl.$^7$ .......................... A61C 5/00; A61K 6/027; A61K 7/16; B09K 3/00; C03C 3/078

(52) U.S. Cl. ...................... 424/49; 106/35; 433/217.1; 433/228.1

(58) Field of Search ................. 424/49–58; 106/35; 433/217.1, 228.1

(56) References Cited

U.S. PATENT DOCUMENTS

| | | | |
|---|---|---|---|
| 4,189,325 A | 2/1980 | Barrett et al. | 106/30 |
| 4,725,234 A | 2/1988 | Ethridge | 433/215 |
| 4,737,411 A | 4/1988 | Graves, Jr. et al. | 106/35 |
| 4,775,592 A | 10/1988 | Akahane et al. | 106/35 |
| 4,783,429 A | 11/1988 | Shibuya et al. | 501/5 |
| 4,839,215 A | 6/1989 | Starling et al. | 428/131 |
| 4,851,046 A | 7/1989 | Low et al. | 106/35 |
| 5,034,353 A | 7/1991 | Shibuya et al. | 501/3 |
| 5,074,916 A | 12/1991 | Hench et al. | 106/35 |
| 5,432,130 A | 7/1995 | Rheinberger et al. | 501/32 |
| 5,584,693 A | * 12/1996 | Nishihara | 433/169 |
| 5,681,872 A | 10/1997 | Erbe | 523/114 |
| 5,728,753 A | * 3/1998 | Bunfield | 523/114 |
| 5,735,942 A | 4/1998 | Litkowski et al. | 106/35 |
| 5,891,233 A | 4/1999 | Salonen et al. | 106/35 |
| 5,977,204 A | * 11/1999 | Boyan et al. | 523/113 |
| 6,051,247 A | * 4/2000 | Hench et al. | 424/423 |
| 6,054,400 A | * 4/2000 | Brink et al. | 501/63 |
| 6,086,374 A | * 7/2000 | Litkowski, II et al. | 433/217.1 |

FOREIGN PATENT DOCUMENTS

| | | |
|---|---|---|
| JP | 73-00339 | 11/1975 |
| JP | 8-048539 | 2/1996 |
| JP | 8-012512 | 11/1996 |
| WO | WO 99/121628 | 7/1996 |
| WO | WO 97/27148 | 7/1997 |
| WO | WO 99/13852 | 3/1999 |

OTHER PUBLICATIONS

*Absi, et al., "Dentine hypersensitivity: uptake of toothpastes onto dentine and effects of brushing, washing and dietary acid—SEM in vitro study", 22 *J. of Oral Rehabilitation* 175–182 (1995).

*Addy, et al., "Dentyne hypersensivity. II Effects produced by the uptake in vitro of toothpastes on dentine", 16 *J. of Oral Rehabilitation* 35–48 (1989).

Anderson, "The Bioactivity of Silicate Glass", Thesis, Dept of Chem Engineering, Åbo Akademi University, Finland (1990).

Larmas, et al., "Bioactive Glass in Periodontal Bone Defects. Initial Clinical Findings of Soft Tissue and Osseus Repair", 8 *Bioceramics* 279–284 (1995).

Yamashita, et al., "Effect of Calcium Ions on Cell Surface Electrostatics of Bacteroides gingivalis and Other Oral Bacteria", 275 *Zentralblatt fur Bateriologie.* 46–53 (1991).

Greenwood, "Morphology and Nature of Micro–organisms", *Medicinal Microbiology* 11–30 (14th ed., 1992).

Nolte, "Physiology and Growth of Microorganisms", *Oral Microbiology* 25–38 (3rd ed., 1977).

Slots, "The predominant cultivable microflora of advanced periodontitis", 85 *Scand. J. Dent. Res.* 114–121 (1977).

Slots, "The predominant cultivable organisms in juvenile periodontitis", 84 *Scand. J. Dent. Res.* 1–10 (1976).

Wilson et al., "Clinical Application of Bioglass Implants", 7 *Bioceramics* 415–422 (1994).

Aitasalo, et al, "Behaviour of Bioactive Glass (S53P4) in Human Frontal Sinus Obliteration", 10 *Bioceramics* 429–432 (1997).

Cimasoni et al., *Crevicular Fluid Updated,* 70–71 (2nd ed., 1983).

Burnett et al., "Dental Caries", *Oral Microbiology and Infectious Disease* 193–197 (1978).

Andersson et al., "Dissolution, Ieaching, and $Al_2O_3$ enrichment at the surface of bioactive glasses studied by solution analysis", 27 *J. Biomed. Mat. Res.* 941–948 (1993).

Hench et al., "Direct Chemical Bond of Bioactive Glass–Ceramic Materials to Bone and Muscle", 4 *J. Biomed. Mater. Res. Symposium* 25–42 (1973).

(List continued on next page.)

*Primary Examiner*—Shep K. Rose
(74) *Attorney, Agent, or Firm*—James C. Lydon

(57) ABSTRACT

The invention relates to a method for reducing the viability of detrimental oral microorganisms in an individual, said method comprising subjecting the individual's oral cavity to a bioactive glass, the average particle size of which is less than 100 $\mu$m. Furthermore, this invention concerns a method for the prevention of dental caries and/or gingivitis in an individual, said caries being caused by a cariogenic bacteria; or for prevention or treatment of periapical infections. Further the invention relates to a method for the whitening and/or mechanical cleaning of an individual's teeth.

7 Claims, 2 Drawing Sheets

OTHER PUBLICATIONS

Morrier et al., "Antibacterial action of dental cements: An in vitro study", 38 *Bull Group Int Rech Sci Stomatol et Odontal,* 87–93 (1995).

Tanner, et al., "A study of the bacteria associated with andvancing periodontitis in man", 6 *J. Clinical Periodontology* 278–307 (1979).

Spiegel, et al., "Black–pigmented Bacteroides from clinically characterized periodontal sites", 14 *J. Periodontal Res.* 376–382 (1979).

Barbosa, et al., "Low surface tension calcium hydroxide solution is an effective antiseptic", 27 *Int'l Endodontic J.* 6–10 (1994).

Newman, et al., "Studies of the Microbiology of Periodontosis", 47 *J. Periodontal* 373–379 (1976).

Syed et al., "Survival of Human Dental Plaque Flora in Various Transport Media", 24 *Applied Microbiology* 638–644 (1972).

Salonen, et al., "Mineralization of Dentin by Making Use of Bioactive Glass S53P4", *Biomaterials Today and Tomorrow—Proc. of the Finnish Dental Society* 25–26 (1996).

Suominen et al., "Bioactive Glass Granules and Plates in the Reconstruction of Defects of the Facial Bones", 30 *Scand. J. Plast. Reconstr. Surg. Hand Surg.* 1–11 (1996).

Drake, et al., "Enhanced Bacterial activity of Arm and Hammer Dental Care", 8 *Amer. J. of Dent.* 308–312 (1995).

Stoor et al., "Antibacterial Effects of a Bioactive Glass Paste on Oral Microorganisms", *ACTA Odontol. Scand.* 56 (1998).

Stoor et al., "Interactions Between Bioactive Glass and Periodontal Pathogens", 9 *Microbial Ecology in Health and Disease.* 109–114 (1996).

Stoor et al., "Interactions Between the Frontal Sinusitis–Associated Pathogen *Haemophilus Influenzae* and the Bioactive Glass S53P4", 8 *Bioceramics.* 253–258 (1995).

*Slots et al., "*Bacteroides gingaivalis, Bacteroides intermedius* and *Actinobacillus actinocetermcomitans* in Human Periodontal Diseases", 15 *J. Clin. Periodontol.* 85–93 (1988).

*Caulfied, "Dental Caries—A Transmissible and Infectious Disease Revisited: A Position Paper", 19 *Amer.Acad.Pediatric Dentistry* 491–498 (1997).

* cited by examiner

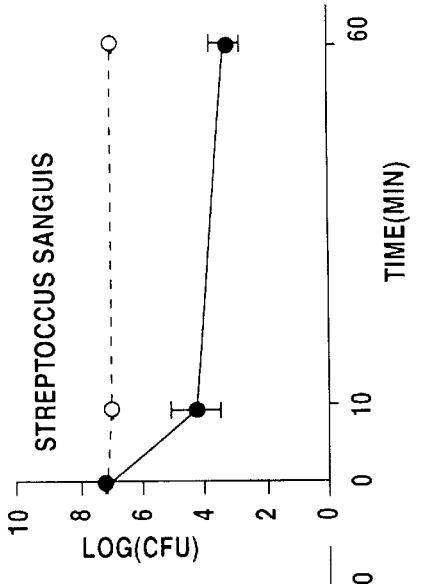
FIG.1C STREPTOCCUS SANGUIS
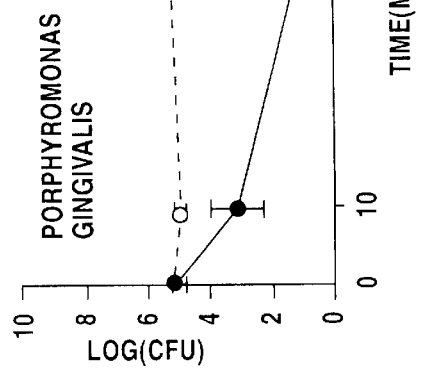
FIG.1B PORPHYROMONAS GINGIVALIS
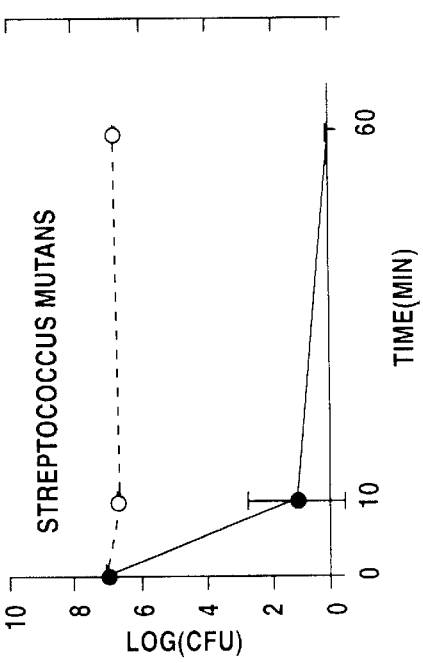
FIG.1E STREPTOCOCCUS MUTANS
FIG.1A ACTINOBACILLUS ACTINOMYCETEMCOMITANS
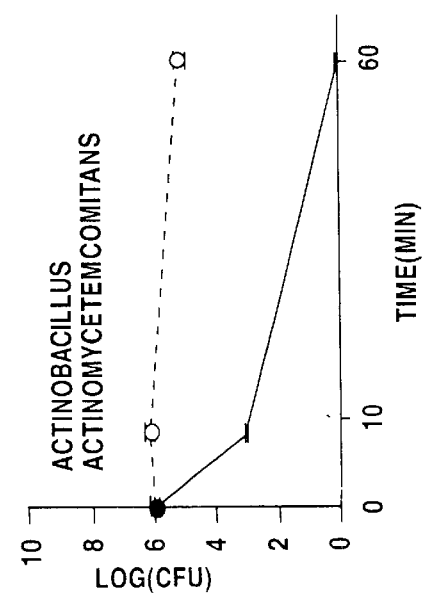
FIG.1D ACTINOMYCES VISCOSUS
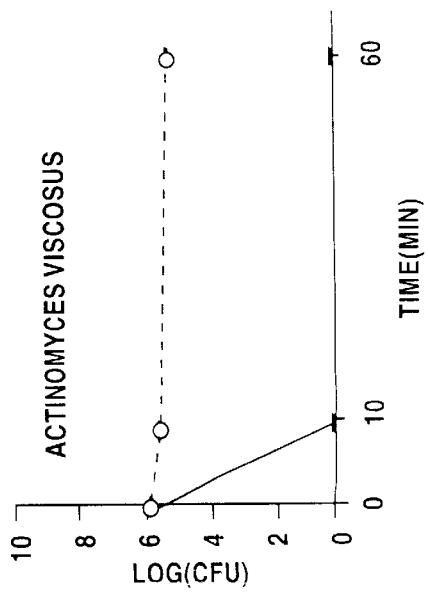

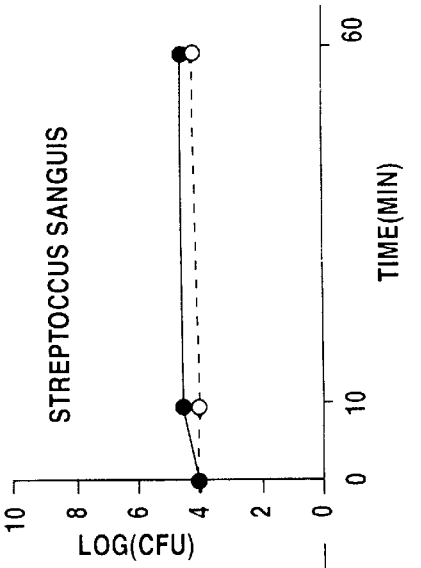
FIG.2A
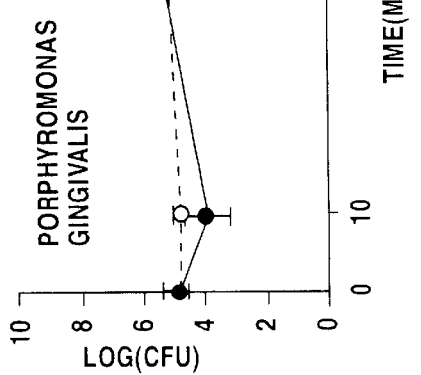
FIG.2B
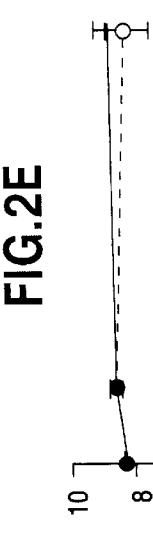
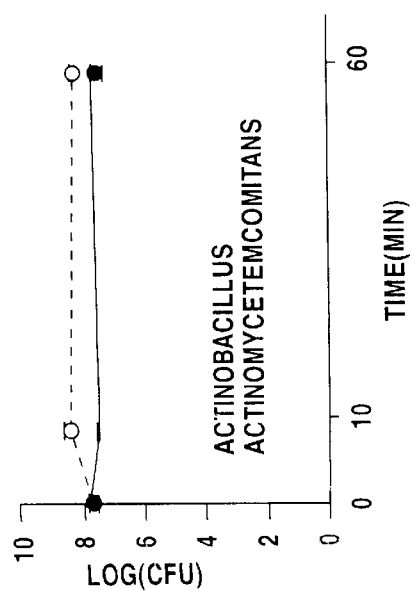
FIG.2D
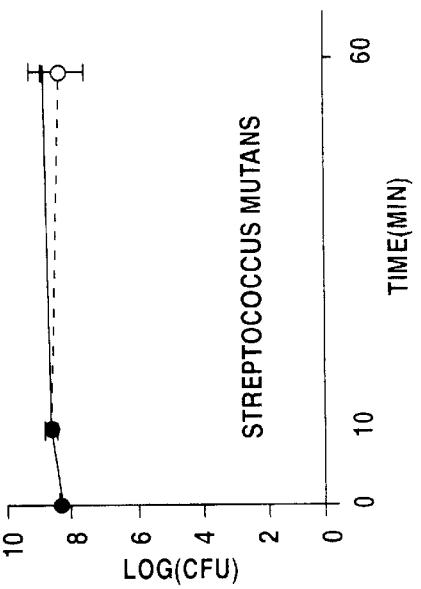
FIG.2C
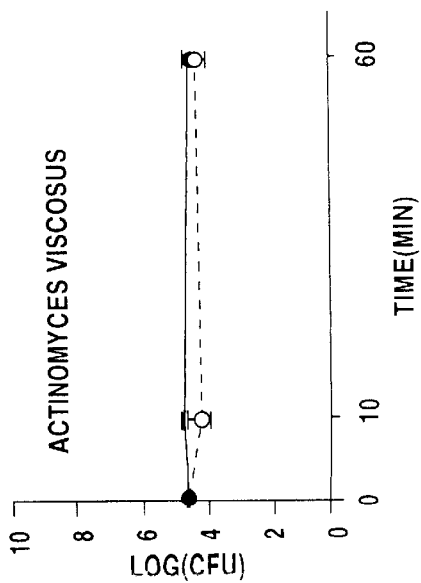
FIG.2E

METHOD FOR REDUCING THE VIABILITY OF DETRIMENTAL ORAL MICROORGANISMS IN AN INDIVIDUAL, AND FOR PREVENTION AND/OR TREATMENT OF DISEASES CAUSED BY SUCH MICROORGANISMS; AND WHITENING AND/OR CLEANING OF AN INDIVIDUAL'S TEETH

This application is a division of application Ser. No. 09/260,081, filed Mar. 2, 1999 and now U.S. Pat. No. 6,190,643.

FIELD OF THE INVENTION

This invention relates to a method for reducing the viability of detrimental oral microorganisms in an individual, and for prevention of dental caries and gingivitis, and for prevention or treatment of periapical infections, and whitening and/or mechanical cleaning of an individual's teeth.

BACKGROUND OF THE INVENTION

The publications and other materials used herein to illuminate the background of the invention, and in particular, cases to provide additional details respecting the practice, are incorporated by reference.

Bioactive glasses have been tested as substitutes for reconstruction of defects of the facial bones (1), rehabilitation of the dentoalveolar complex (2), regeneration of periodontal pockets (3), and recently also for treatment of hypersensitive teeth (4). The surface reactive bioactive glass contains $SiO_2$, $Na_2O$, $CaO$ and $P_2O_5$. The chemical bond with bone in vivo is reported to result from the leaching of $Na^+$-ions and the congruent dissolution of calcium, phosphate and silica from the glass in an aqueous environment, giving rise to an Si-rich layer on the material. The Si-rich layer acts as a templet for a calcium phosphate precipitation, which then binds to the bone (5). Bioactive glass has been successfully used for reconstructions of closed bone defects, which are not exposed to the external environment after the clinical procedure (1). However, there are a number of conditions for which bioactive glasses are used as therapeutic materials but that, at the same time, are imminently prone to microbial infections. These include clinical conditions such as infected frontal sinuses (6), periodontal pockets (3) and hypersensitive teeth as a complication of periodontal treatment or tooth wear that has resulted in the exposure of dentin and dentinal tubules (4). Obviously, the demonstration of any antibacterial activity of the biactive glass would add to the therapeutic value of the material in the clinical conditions described. Earlier studies have shown that *P. gingivalis* is agglutinated in the presence of granules (315–500 µm) of the bioactive glass S53P4 in an aqueous environment due to $Ca^{+2}$-ions released from the granules (19,7). The minimum $Ca^{2+}$-concentration needed to induce agglutination of *P. gingivalis* was found to be 0.04 g/l (7). In these studies, however, no reduction of the viability of the bacteria was noticed.

Earlier studies have shown that the bioactive glass can act as a vehicle for $Ca^{2+}$, $PO_4^{3-}$, $Na^+$ and $Si^{4+}$, which then mineralise type I collagen and enhance mineral formation in the dentinal tubules. Therefore, an aqueous preparation comprising bioactive glass may have potential to be used as a paste for the treatment of hypersensitive teeth with recessed gingival margins and exposed dentine. Positive effects of such a treatment have been obtained already after 10 to 60 min, which makes this particular material interesting even from a clinical point of view (4).

OBJECT AND SUMMARY OF THE INVENTION

The object of the present invention is to provide an easy, quick and safe method to reduce the viability of detrimental oral microorganisms in an individual. A particular object is to achieve a method which is not based on use of antibiotic drugs associated with the risk of causing microbe resistance.

A particular object is to provide a method to reduce the viability of cariogenic bacteria and periodontal bacteria.

Another particular object is to provide a method to effectively reduce the viability of the detrimental oral microorganisms while the viability of non-pathogenic oral microorganisms is reduced to a lesser degree.

A further object of this invention is to provide methods for prevention of dental caries and/or gingivitis, and for whitening of an individual's teeth, wherein said methods are due to the reduction of the viability and thus the decrease of the number of the detrimental oral micro-organisms.

Still another object is to achieve mechanical cleaning and whitening of an individuals teeth, wherein the whitening is a result of said mechanical cleaning.

Thus, according to one aspect, the invention concerns a method for reducing the viability of detrimental oral microorganisms in an individual, said method comprising subjecting the individual's oral cavity to a bioactive glass, the average particle size of which is less than 100 µm.

According to another aspect, the invention concerns a method for the prevention of dental caries and/or gingivitis in an individual, said caries being caused by a cariogenic bacteria, or for prevention or treatment of periapical infections, said method comprising subjecting the individual's oral cavity and/or root canals to a bioactive glass, the average particle size of which is less than 100 µm.

According to a further aspect, this invention concerns a method for the whitening of an individual's teeth, said method comprising subjecting the individual's oral cavity to a bioactive glass, the average particle size of which is less than 100 µm.

BRIEF DESCRIPTION OF THE DRAWINGS

FIGS. 1A to 1E show the effect of 1) the powdered bioactive glass S53P4 (continuous lines) and 2) control containing no bioactive glass (dashed lines) on the number of viable microbes in suspension. Values shown are means; bars indicate range; n=3. CFU=colony-forming units.

FIGS. 2A to 2E show the effect of 1) $SiO_2$ powder (continuous lines) and 2) control containing no $SiO_2$ powder (dashed lines) on the number of viable counts microbes in suspension. Values shown are means; bars indicate range; n=2 to 3. CFU=colony-forming units.

DETAILED DESCRIPTION OF THE INVENTION

The term "reducing the viability of detrimental oral microorganisms" shall be understood to include reduction to a certain decreased level as well as reduction to zero, i.e. complete elimination of viable microorganisms.

The term "average particle size" means that 50% of the number of particles have a size less than or equal to the value mentioned (e.g. 100 µm) and that 50% of the number of particles have a size greater than or equal to said value.

According to a preferred embodiment, the average particle size is below 50 µm, most preferably about 20 µm or less. The size of the individual particles may vary in a range extending from a value below 1 µm up to about 500 µm.

The "oral cavity" to be treated according to this invention means particularly the individual's teeth and periodontal regions in the mouth. Especially the individual's teeth down to the gingival margin and/or the periodontal pockets the individual's mouth shall be treated, as well as root canals in endodontic treatment.

The bioactive glass is preferably administered as a composition comprising particles of the bioactive glass admixed into water or an aqueous solution. Especially preferable is a paste comprising about 40 to 80 weight-% of bioactive glass. The composition can optionally also include other ingredients. According to an especially preferable embodiment, the composition is a tooth paste for regular use, including the bioactive glass.

Some typical and preferable bioactive glass compositions are presented in Table 1.

TABLE 1

Composition (weight-%) of some bioactive glass types 1–17

| Glass | Type | $Na_2O$ | CaO | $P_2O_5$ | $B_2O_3$ | $Al_2O_3$ | $SiO_2$ |
|---|---|---|---|---|---|---|---|
| 1 | S63.5P6 | 15.00 | 14.00 | 6.00 | 0.50 | 1.00 | 63.50 |
| 2 | S57.5P5 | 16.00 | 18.00 | 5.00 | 3.00 | 0.50 | 57.50 |
| 3 | S65.5P1 | 17.00 | 13.00 | 1.00 | 1.00 | 2.50 | 65.50 |
| 4 | S52P3 | 18.00 | 24.00 | 3.00 | 0.00 | 3.00 | 52.00 |
| 5 | S56P6 | 19.00 | 16.00 | 6.00 | 1.50 | 1.50 | 56.00 |
| 6 | S51P7 | 20.00 | 17.00 | 7.00 | 3.00 | 2.00 | 51.00 |
| 7 | S51P2 | 21.00 | 21.00 | 2.00 | 2.00 | 3.00 | 51.00 |
| 8 | 564P0 | 22.00 | 10.00 | 0.00 | 2.50 | 1.50 | 64.00 |
| 9 | S53P4 | 23.00 | 20.00 | 4.00 | 0.00 | 0.00 | 53.00 |
| 10 | S45P7 | 24.00 | 22.00 | 7.00 | 2.00 | 0.00 | 45.00 |
| 11 | S52P8 | 25.00 | 12.00 | 8.00 | 0.50 | 2.50 | 52.00 |
| 12 | S46P0 | 26.00 | 25.00 | 0.00 | 2.00 | 1.00 | 46.00 |
| 13 | S38P8 | 27.00 | 23.00 | 8.00 | 1.00 | 3.00 | 38.00 |
| 14 | S48P2 | 28.00 | 19.00 | 2.00 | 1.50 | 1.50 | 48.00 |
| 15 | S55.5P4 | 29.00 | 11.00 | 4.00 | 0.00 | 0.50 | 55.50 |
| 16 | S45.5P5 | 30.00 | 15.00 | 5.00 | 2.50 | 2.00 | 45.50 |
| 17[x)] | 13–93 | 6.00 | 20.00 | 4.00 | 0.00 | 0.00 | 53.00 |

[x)]this glass contains in addition 12% of $K_2O$ and 5% of Mgo (weight-%).

Particularly preferable bioactive glasses are the glass S53P4, which has the composition $SiO_2$ 53%; CaO 20%; $P_2O_5$ 4% and $Na_2O$ 23%, and the glass 13–93, which has the composition $SiO_2$ 53%; CaO 20%; $P_2O_5$ 4%, $Na_2O$ 6%, $K_2O$ 12% and MgO 5%.

The method according to the invention is particularly effective to reduce the viability of cariogenic bacteria, especially Actinomyces naeslundii and/or Streptococcus mutans. Also periodontal bacteria (i.e. bacteria causing gingivitis). Typical periodontal bacteria are Actinobacillus actinomycetemcomitans and/or Porphyromonas gingivalis. However, the reduction of the viability of non-pathogenic oral bacteria such as Streptococcus sanguis is lower than that for the detrimental oral microorganism. This is a very favourable feature, because essential reduction of the non-pathogenic oral bacteria is not wanted.

The duration of the treatment depends i.a. on the particular bioactive glass composition used, the average particle size, the bacteria in question, etc. As will be seen from the experimental data, a period of about 10 minutes may be enough to effectively eliminate viable cariogenic bacteria (bioactive glass S53P4, average particle size 20 µm), while a longer treatment is necessary for periodontal bacteria.

Oral bacteria are known to cause discolouring of teeth, as also coffee, tea, tobacco etc. Bioactive glass is therefore, as an effective antibacterial agent and as a mechanically cleaning agent, useful for cleaning and whitening of the teeth.

The invention is described in more detail in the Experimental Section.

Experimental Section

The purpose of this study was to examine the antibacterial effects of a paste made of the bioactive glass S53P4 (8) on oral microorganisms representing periodontal pathogens, caries-associated microorganisms and benign oral microflora. Two major pathogens were used: Actinobacillus actinomycetemcomitans, which has been suggested to play a role in juvenile periodontitis (9,10), and Porphyromonas gingivalis, which has been associated with destructive periodontal lesions in adults (11, 12, 13). Also were studied Actinomyces naeslundii, which is associated with root caries; Streptococcus mutans, which is considered to play a major role in caries; and Streptococcus sanguis as a representative of the benign oral microbiota (14).

Materials and Methods

Materials

The bioactive glass powder S53P4 used in this study was produced by Abmin Technologies Ltd, Turku, Finland. The composition of the bioactive glass S53P4 given by weight is: $SiO_2$ 53%, $Na_2O$ 23%, CaO 20% and $P_2O_5$ 4%. The bioactive glass was prepared from reagent grade $Na_2CO_3$, $CaHPO_4 \times 2H_2O$, $CaCO_3$ (Merck, Darmstadt, Germany) and Belgium sand. The glass batches were melted for 3 h at 1360° C. After melting, the glass was cast into a plate, which was cooled from 520° C. to 220° C. at 1° C./min in an annealing oven. The oven was turned off and air-cooled to room temperature. The plate was crushed and dry ground in an agate mill. Powder, of particle size <45 µm, (average particle size 20 µm), was sieved out of the batch (8).

The powder was combined with a microbial suspension using a ratio of glass powder and liquid (50 mg and 30 µl, respectively), simulating the composition used for treatment of hypersensitive teeth (4).

As controls we used 1) no added glass powder and 2) an inert $SiO_2$ powder, containing 100% $SiO_2$, of particle size <45 µm (Biomaterials project, Institute of Dentistry, University of Turku, Finland).

Microorganisms

The microorganisms used were Actinobacillus actinomycetemcomitans (ATCC 29523), Porphyromonas gingivalis (ATCC 33277), Actinomyces naeslundii (clinical isolate), Streptococcus mutans (NCTC 10449) and Streptococcus sanguis (NCTC 10904).

Preparation of the Microbial Suspensions

Precultivation of A. actinomycetemcomitans, S. mutans and S. sanguis was performed at 37° C. in BHI (Brain Heart Infusion, Unipath Ltd, Hampshire, England). After approximately 18 h of growth, the cells were washed once in saline (S. mutans and S. sanguis) or in Reduced Transport Fluid (RTF: 0.6 g/l $K_2HPO_4 \times 3H_2O$, 0.23 g/l NaCl, 0.23 g/l $(NH_4)_2SO_4$, 0.11 g/l $KH_2PO_4$, 0.1 g/l $MgSO_4 \times 7H_2O$, 0.37 g/l disodium ethylenedinitrilo tetraacetate; $C_{10}H_{14}N_2Na_2O_8 \times 2H_2O$, 0.4 g/l $Na_2CO_3$, 0.2 g/l dithiothreitol; $C_4H_{10}O_2S_2$) (15) (A. actinomycetemcomitans). The suspensions were adjusted with saline or RTF to an optical density of approximately 1.0 [$A_{700}$; corresponding to $10^5$–$10^7$ colony forming units, (CFU)/ml]. P. gingivalis was precultivated anaerobically (80% $N_2$, 10% $CO_2$, 10% $H_2$) at 37° C. on Brucella agar plates (Difco Laboratories, Detroit, USA). The cells were harvested after 6 days' growth, washed once in Brewer Thioglycollate medium (500 g/l Beef Infusion, 5 g/l NaCl, 2 g/l $K_2HPO_4$, 10 g/l Proteose Peptone, 5 g/l Bacto Dextrose, 0.5 g/l Na-Thioglycollate, 0.5 g/l Bacto Agar, 0.002 g/l Bacto Methylene Blue) and finally adjusted with Brewer Thioglycollate medium to an optical density of approximately 1.0 ($A_{700}$; corresponding to $10^4$–$10^5$ CFU/ml). *A. naeslundii* was precultivated in Brewer Thioglycollate medium (Difco) at 37° C. for 3 days, washed once in RTF and adjusted with RTF to a density of approximately 1.0 ($A_{700}$; corresponding to $10^5$–$10^6$ CFU/ml).

Incubation Experiments

The bioactive glass powder (50 mg) and 30 μl of the microbial suspension were first vortexed for thorough mixing for 10 min at room temperature in Eppendorf tubes (Sarstedt, Germany), followed by incubation without agitation for 50 min at 37° C. The controls contained 1) no added bioactive glass powder or 2) 50 mg inert $SiO_2$ powder (particle size <45 μm).

For assessment of viability as CFU, the incubation was stopped by adding 470 μl RTF (*A. actinomycetemcomitans, P. gingivalis, A. naeslundii*) or saline (*S. mutans, S. sanguis*), followed by vortexing and gentle sonication for 2 s to detach the microorganisms from the bioactive glass powder and from the inert $SiO_2$ powder. The assessment of viability as CFU of the microbial suspensions was performed on solid growth media by cultivating 10 μl samples from the suspensions diluted in saline ($10^1$–$10^7$). The undiluted suspension was also cultivated by using 20 μl samples. *A. actinomycetemcomitans* and *A. naeslundii* were cultivated on blood agar anaerobically at 37° C. for 3 days and approximately 18 h, respectively. *P. gingivalis* was cultivated anaerobically at 37° C. for 6 days on Brucella agar plates. *S. mutans* and *S. sanguis* were cultivated on Mitis salivarius agar for approximately 18 h at 37° C. aerobically in an atmosphere consisting of 74% $N_2$, 19% $O_2$ and 7% $CO_2$. The experiment was performed with 2–3 parallels and repeated once.

Ion release from the bioactive glass paste and related pH changes

The release of ions from the bioactive glass powder (50 mg) during the 60 min contact with saline (30 μl) was analyzed with a Direct Current Plasma Atomic Emission Spectroscopy DCP-AES at the Department of Chemistry at Åbo Akademi University, Turku, Finland. The determinations were performed in triplicate. After the vortexing (10 min) and incubation (50 min) the samples were suspended in 5 ml laboratory grade $H_2O$ (Milli-QUF PLUS, Millipore, Molsheim, France), rapidly mixed and immediately filtrated with a Millex-GS 0.22 mm filter (Millipore).

The time-dependent changes in the pH values of saline and Brewer Thioglycollate medium were monitored after 10-min and 60-min incubation with the bioactive glass powder. The measurements were performed with a combination electrode pHC4406 (Radiometer, Copenhagen, Denmark).

Results

The time-dependent release of calcium, phosphorous, silica and sodium from the bioactive glass paste is given in Table 2. For calcium, phosphorous and sodium, the amount of released ions did not increase during the prolonged incubation, but for silica the amount tripled during the 10–60-min incubation. The increased osmotic pressure was created mostly by an almost immediate release of high amounts of sodium, which corresponds to a concentration of 3.38% at 10 min and 3.50% at 60 min.

TABLE 2

Measurements of the release of four elements from the bioactive glass S53P4 in powdered form, showing almost instant release of calcium, phosphorous and sodium. The amount of released silicon tripled during the time period, 10–60 min. The values shown are means ± standard deviations (s) in mg/l.

| Element | 10 min Mean | | s | 60 min Mean | | s |
|---|---|---|---|---|---|---|
| Ca | 2990 | ± | 210 | 3520 | ± | 190 |
| P | 170 | ± | 30 | 160 | ± | 000 |
| Si | 1440 | ± | 120 | 4740 | ± | 50 |
| Na | 33790 | ± | 540 | 34980 | ± | 220 |

During the incubation with bioactive glass powder, the mean (± standard deviation) of the pH of both the saline and the Brewer Thioglycollate medium increased in 10 min from 6.9 (±0.3) to 10.8 (±0.1). No further increase of the pH was seen.

*A. actinomycetemcomitans* totally lost its viability in contact with the bioactive glass powder within 60 min. A major decrease in the number of viable microbes was already seen within 10 min, as the number of viable microbes decreased from $9 \times 10^5$ to $9 \times 10^2$. Also *P. gingivalis* lost its viability in contact with the glass powder within 60 min. After 10 min, a decrease from $9 \times 10^4$ to $1 \times 10^3$ in the number of viable cells was seen. *S. mutans* lost its viability almost totally, from $6 \times 10^6$ to $0.8 \times 10^1$, after 10 min incubation with the bioactive glass powder. A total loss of viability of *A. naeslundii* was also seen already after 10 min. *S. sanguis* showed a significant loss of viability, at 10 min, from $7 \times 10^6$ to $1 \times 10^4$ and at 60 min, further down to $1 \times 10^3$. (FIG. 1). However, *S. sanguis* was the only microbe that had any viable cells left after 60 min.

The incubations with the reference material, the inert $SiO_2$ powder, showed results similar to those of the controls with no glass powder (FIG. 2).

Discussion

In this study the bioactive glass paste showed a broad antibacterial effect on the microorganisms tested. The effect found may be due to several influences including high pH, osmotic effects and the $Ca^{2+}$-concentration (7).

Since the bioactive glass S53P4 reacts in a surface reactive manner in an aqueous environment, the release of ions and consequently the rise of the pH increases with an increasing surface area of the glass. In the form of a powder (<45 μm) the surface area of the glass is large per weight unit, and thus the release of ions is high. In our experiments the surface area/volume (SA/V) ratio was very high, approximately 1920 $cm^{-1}$. Earlier experiments with bioactive glass S53P4 granules (297–500 μm) where the SA/V ratio was 0.4 $cm^{-1}$ showed almost a linear increase in release of ions during the first 7 hours (16). Owing to the high SA/V ratio in the present experiment the release of ions was up to ×300 times greater during the 60 min incubation than in the earlier experiments with granules (60 min: Ca 24 mg/l, P not detected, Si 15 mg/l, Na 12 mg/l) (16). Thus, the release of ions was faster from the bioactive powder than from the granules. Also the pH change observed with the <45-μm glass powder within 60 min (pH 7→11) was higher than that reported with granules earlier (pH 7→9) (8).

Most heterotrophic bacteria grow well in media with an osmotic pressure created by 0.75% salt. Concentrations higher than 1% become inhibitory for most bacteria. However, many streptococci of the oral cavity can grow well on a 5% sucrose medium, while the growth of most other oral bacteria is inhibited under such conditions (17). As judged by the concentrations of the separate ions released from the glass powder, the total osmotic pressure was, already after 10 min, created by a concentration higher than 3% and, after 60 min, by a concentration above 4% (see Table 2). Since the outer membrane of gram-negative bacteria. (*A. actinomycetemcomitans, P. gingivalis*) is reported to be a more efficient permeability barrier than the cell wall of the gram-positive bacteria (*A. naeslundii, S. mutans, S. sanguis*) (18), the osmotic effects due to the bioactive glass paste could partly explain the relative resistance of the gram-negative microorganisms and the more rapid loss of viability of *A. naeslundii* and *S. mutans*. Because *S. sanguis*, despite the lack of an effective permeability barrier, was the only microbe that managed to maintain some viability also other mechanisms must be involved.

The $Ca^{+2}$-ion concentration measured in association with the paste of bioactive glass powder used in this study was much higher (3.0–3.5 g/l) than that shown (0.04 g/l) in the earlier study (7) using granules (315–500 μm) of the same bioactive glass.

In addition to the immediate antibacterial effect due to the instant release of ions from the bioactive glass, possible residues of bioactive glass cause long term effects over days and even months, due to the continuing leaching of ions from the bioactive glass.

In conclusion, the bioactive glass paste appears to possess a broad antimicrobial effect on microorganisms of both supra- and subgingival plaque. Consequently, the bioactive glass paste may have beneficial effects on oral health both from a cariological and a periodontal point of view, in addition to its more direct therapeutic effect on root surface hypersensivity. Apparently, the clinical benefits of the bioactive glass powder when used as a paste or as a component in toothcare products come from a combination of good influences rather than from any single property, such as its ability to reduce bacterial growth. These influences include mechanical cleaning and remineralisation of both dentine and enamel.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

1. Suominen E A, Kinnunen J. Bioactive glass granules and plates in the reconstruction of defects of the facial bones. Scand J Plast Reconstr Surg Hand Surg 1996;30:281–9.
2. Wilsin J, Clark A E, Douek E, Krieger J, Smith W K, Zamet J S. Clinical applications of bioglass implants. In: Andersson ÖH, Happonen R-P, editors. Bioceramics Vol 7. Cambridge: Butterworth-Heinemann Ltd; 1994. p. 415–22.
3. Larmas E, Sewón L, Luostarinen T, Kangasniemi I, Yli-Urpo A. Bioactive glass in periodontal defects. Initial clinical findings of soft tissue and osseus repair. In: Wilson J, Hench L L, Greenspan D, editors. Bioceramics Vol 8. Oxford: Elsevier Science Ltd; 1995. p. 279–84.
4. Salonen J, Tuominen U, Andersson ÖH. Mineralization of dentine by making use of bioactive glass S53P4. In: Andersson ÖH, Salonen J, Yli-Urpo A, editors. Biomaterials Today and Tomorrow, Proceedings of the Finnish Dental Society. Turku: Turku Centre for Biomaterials; 1996. p. 25–6.
5. Hench L L, Paschall H A. Direct chemical bond of bioactive glass-ceramic materials to bone and muscle. J Biomed Mater Res 1973;7:25–42.
6. Aitasalo K, Suonpää J, Peltola M, Yli-Urpo A. Behaviour of bioactive glass (S53P4) in human frontal sinus obliteration. Sedel L, Rey C, editors. Bioceramics Vol 10. Oxford: Elsevier Science Ltd; 1997. p. 429–32.
7. Stoor P, Kirstilä V, Söderling E, Kangasniemi I, Herbst K, Yli-Urpo A. Interactions between bioactive glass and periodontal pathogens. Microb Ecol Health Dis 1996;9:109–14.
8. Andersson Ö. The bioactivity of a Silicate Glass. Thesis, Åbo Akademi University, Finland; 1990.
9. Newman M G, Socransky S S, Savitt E D, Propas D A, Crawford A. Studies of the microbiology of periodontitis. J Periodont 1976;47:373–79.
10. Slots J. The predominant cultivable organisms in juvenile periodontitis. Scand J Dent Res 1976;84:1–10.
11. Slots J. The predominant cultivable microflora of advanced periodontitis. J Dent Res 1977;85:114–21.
12. Spiegel C A, Hayduk E S, Minah G E, Kryoplan G N. Black pigmented bacteroides from clinically characterized periodontal sites. J Periodont Res 1979;14:376–82.
13. Tanner A C R, Haffer C, Bratthall G T, Visconti R A, Socransky S S. A study of the bacteria associated with advancing periodontal disease in man. J Clin Periodont 1979;6:278–307.
14. Burnett G W, Schuster G S. Oral microbiota and its disease. In: Burnett G W, Schuster G S, editors. Oral microbiology and infectious disease. Student edition. Baltimore: The Williams & Wilkins Company; 1978. p. 174–253.
15. Syed S A, Loesche W J. Survival of human dental plaque flora in various transport media. Appl Microbiol 1972;24:638–44.
16. Andersson ÖH, Rosenqvist J, Karlsson K H. Dissolution, leaching, and $Al_2O_3$ enrichment at the surface of bioactive glasses studied by solution analysis. J Biomed Mater Res 1993;27:941–48.
17. Nolte W A. Physiology and growth of microorganisms. In: Nolte W A, editor. Oral Microbiology with basic microbiology and immunology. 3rd ed. St. Louis: The C.V. Mosby Company; 1977. p. 25–38.
18. Greenwood D. Morphology and nature of microorganisms. In: Greenwood D, Slack R, Peutherer J, editors. Medical Microbiology. 14th ed. Churchill Livingstone: Longman Group UK Limited; 1992. p. 11–30.
19. Yamashita Y, Kunimori A, Takehara T. Effect of Ca ions on cell surface electrostatics of Bacterioides gingivalis and other oral bacteria. Zentralblatt für Bacteriologie 1991;275:46–53.
20. Cimasoni G. In: Myers H, editor. Crevicular Fluid Updated. 2nd ed. Basel: Krager; 1983. p. 70–1.
21. Barbosa S V, Spangberg S W, Almedia D. Low surface tension calcium hydroxide solution is an effective antiseptic. Int Endod J 1994;27:6–10.
22. Drake D R, Vargas K, Cardenzana A, Srikantha R. Enhanced bactericidical activity of Arm and Hammer Dental Care. Am J Dent 1995;8:308–12.
23. Morrier J J, Rocca J P, Barsotti O. Antibacterial action of dental cements. Bull Group Int Rech Sci Stomatol Odontol 1995;38:87–93.

What is claimed is:

1. A method for the prevention or treatment of dental caries, or gingivitis or a periapical infection in an individual in need of such prevention or treatment, said method comprising subjecting the individual's oral cavity or root canals to a bioactive glass, the average particle size of which is less than 100 um.

2. The method according to claim 1, wherein the average particle size is less than 50 μm, preferably about 20 μm or less.

3. The method according to claim 1, wherein the bioactive glass is administered as a composition comprising particles of the bioactive glass admixed into water or an aqueous solution.

4. The method according to claim 3, wherein the composition is a paste comprising about 40 to 80 weight-% of bioactive glass.

5. The method according to claim 1, wherein the bioactive glass is selected from a bioactive glass having the composition $SiO_2$ 53%; CaO 20%; $P_2O_5$ 4% and $Na_2O$ 23% by weight, or $SiO_2$ 53%; CaO 20%; $P_2O_5$ 4%, $Na_2O$ 6%, $K_2O$ 12% and MgO 5% by weight.

6. The method according to claim 5, wherein the cariogenic bacteria are *Actinomyces naeslundii* and/or *Streptococcus mutans*.

7. The method according to claim 1, wherein the treatment is carried out for about 10 minutes.

* * * * *

UNITED STATES PATENT AND TRADEMARK OFFICE
CERTIFICATE OF CORRECTION

PATENT NO.    : 6,342,207 B1
DATED         : January 29, 2002
INVENTOR(S)   : Stoor et al.

It is certified that error appears in the above-identified patent and that said Letters Patent is hereby corrected as shown below:

Title page,
Item [76], Inventors, change the address of inventor "Jukka Salonen" to read as follows: -- Puolalanpuisto 4b A4, FIN-20100 Turku --.

Column 3,
Table 1, footnote, change "Mgo" to -- MgO --.

Column 5,
Line 35, change "($O_2$" to -- $O_2$ --.

Column 6,
Line 48, change "larce" to -- large --.

Column 8,
Lines 62 and 64, delete "prevention or"; and
Line 65, delete "or root canals"; and
Line 67, change "um" to -- $\mu$m --.

Signed and Sealed this

First Day of July, 2003

JAMES E. ROGAN
*Director of the United States Patent and Trademark Office*